(12) United States Patent
Carmi

(10) Patent No.: US 10,217,247 B2
(45) Date of Patent: Feb. 26, 2019

(54) METHOD FOR GENERATING CONTRAST AGENT CONCENTRATION MAP

(71) Applicant: KONINKLIJKE PHILIPS N.V., Eindhoven (NL)

(72) Inventor: Raz Carmi, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/553,756

(22) PCT Filed: Dec. 8, 2016

(86) PCT No.: PCT/EP2016/080198
§ 371 (c)(1),
(2) Date: Aug. 25, 2017

(87) PCT Pub. No.: WO2017/102529
PCT Pub. Date: Jun. 22, 2017

(65) Prior Publication Data
US 2018/0276853 A1 Sep. 27, 2018

(30) Foreign Application Priority Data
Dec. 17, 2015 (EP) .................................. 15200863

(51) Int. Cl.
*G06K 9/00* (2006.01)
*G06T 11/00* (2006.01)
(Continued)

(52) U.S. Cl.
CPC .............. *G06T 11/003* (2013.01); *A61B 6/03* (2013.01); *A61B 6/481* (2013.01); *A61B 6/484* (2013.01);
(Continued)

(58) Field of Classification Search
CPC ........... A61B 6/032; A61B 6/481; A61B 6/03; G06K 2209/05; G06T 2207/10081; G06T 2207/30004
See application file for complete search history.

(56) References Cited

U.S. PATENT DOCUMENTS 9,055,919 B2 * 6/2015 Proksa ................. A61B 5/4869
2002/0146371 A1 * 10/2002 Li ....................... A61K 49/0002
424/1.73
(Continued)

FOREIGN PATENT DOCUMENTS

WO 2014/097124 6/2014

OTHER PUBLICATIONS

J. R. Ashton et al., "Anatomical and functional imaging of myocardial infarction in mice using micro-CT and eXIA 160 contrast agent" in Contrast Media Mol. Imaging, 2014, 9, pp. 161-168.
(Continued)

*Primary Examiner* — Li Liu

(57) ABSTRACT

Method for generating contrast agent concentration map from a non-contrast enhanced Computed Tomography scan, a contrast enhanced Computed Tomography scan and corresponding spectral Computed Tomography data, comprising: a. Generating at least two different primary contrast agent concentration maps out of the non-contrast enhanced Computed Tomography scan, the contrast enhanced Computed Tomography scan and the spectral Computed Tomography data, b. Performing a local quality analysis of each primary contrast agent concentration map c. Determining local volumetric weights for each primary contrast agent concentration map based on the local quality analysis, and d. Generating a secondary contrast agent concentration map based on the two primary contrast agent concentration maps and on their corresponding local volumetric weights.

15 Claims, 8 Drawing Sheets

(51) Int. Cl.
 A61B 6/00 (2006.01)
 G06T 7/37 (2017.01)
 A61B 6/03 (2006.01)
(52) U.S. Cl.
 CPC .......... A61B 6/5223 (2013.01); A61B 6/5235 (2013.01); G06T 7/37 (2017.01); *G06T 2207/10081* (2013.01); *G06T 2207/20172* (2013.01); *G06T 2207/20224* (2013.01); *G06T 2207/30004* (2013.01)

(56) References Cited

U.S. PATENT DOCUMENTS

| | | | | |
|---|---|---|---|---|
| 2005/0090736 | A1* | 4/2005 | Sommer | A61B 6/481 600/425 |
| 2005/0249329 | A1 | 11/2005 | Kazama | |
| 2007/0217570 | A1* | 9/2007 | Grasruck | A61B 6/032 378/53 |
| 2007/0238968 | A1* | 10/2007 | Rappoport | A61B 6/032 600/407 |
| 2009/0022263 | A1 | 1/2009 | Imai | |
| 2010/0135557 | A1* | 6/2010 | Krauss | A61B 6/032 382/131 |
| 2014/0064589 | A1 | 3/2014 | Dale | |
| 2015/0161792 | A1 | 6/2015 | Li | |
| 2015/0327780 | A1* | 11/2015 | Kano | A61B 5/0261 600/407 |

OTHER PUBLICATIONS

P. M. Cannao et al., "Technical prerequisites and imaging protocols for dynamic and dual energy myocardial perfuaion imaging" in Eur J Radiol, 2015 (Article in Press).

J. He et al., "Dual-energy CT angiography of abdomen with routine concentration contrast agent in comparison with conventional single-energy CT with high concentration contrast agent" in Eur J Radiol, 84, 2015, pp. 221-227.

* cited by examiner

METHOD FOR GENERATING CONTRAST AGENT CONCENTRATION MAP

CROSS REFERENCE TO RELATED APPLICATIONS

This application is the U.S. National Phase application under 35 U.S.C. § 371 of International Application No. PCT/EP2016/080198 filed Dec. 8, 2016, published as WO 2017/102529 on Jun. 22, 2017, which claims the benefit of European Patent Application Number 15200863.7 filed Dec. 17, 2015. These applications are hereby incorporated by reference herein.

The present invention relates to a method for generating contrast agent concentration map. It also relates to a device adapted for communicating with a medical imaging device, to a Computed Tomography scanner and to a Computer readable storage medium.

BACKGROUND OF THE INVENTION

In Computed Tomography applications, contrast agent concentration maps, such as 'iodine maps' which are based on iodine contrast agent or other maps which are based on less common agents such as gadolinium, barium, bismuth or gold, can be very useful in improving the diagnosis accuracy of many diseases and clinical conditions. Two fundamental approaches for generating such iodine maps are known, each method with its pros and cons. One approach utilizes two conventional Computed Tomography scans, with and without contrast agent administration. These scans are also called pre- and post-contrast Computed Tomography scans. By applying volumetric spatial registration followed by image subtraction, the contrast agent map is generated, i.e. the post-contrast image minus the pre-contrast image. The second approach is generating contrast agent map directly from a single spectral Computed Tomography scan. Spectral Computed Tomography, such as dual-energy or photon-counting based, has the ability to quantitatively differentiate contrast agents from biological materials.

There are several advantages of the registration-subtraction method relative to the spectral Computed Tomography technique. First of all, the contrast to noise ratio (CNR) for the same radiation dose is about 3 times higher than in a related dual energy iodine map. This higher CNR can be understood, for example, from the fact that the Hounsfield Unit (HU) difference between the iodine enhancement to the blood or soft tissue HU is about 3 times higher than the difference between the iodine enhancement in the low-energy first-layer image to the high energy second-layer image in dual-layer Computed Tomography (operated at 120 kVp). This comparison includes the consideration that an overall dose equalization between the two techniques brings the original signal to noise of the conventional Computed Tomography image (in the two-scan subtraction protocol) and each of the single-layer images (in the dual-energy single-scan protocol) to about the same level.

Furthermore, in the two-scan protocol, the true non-contrast image is available for clinical diagnostics. This image is usually much better than dual-energy virtual-non contrast image, especially in low-dose Computed Tomography scans.

Besides, in the registration-subtraction technique, the bone and calcium identification and elimination can sometimes be done much more accurately than in single-scan spectral Computed Tomography. This is due to the contrast agent concentration largely varying between the pre- and post-contrast scans as opposed to the bone and calcium remaining the same.

Eventually, dual-energy iodine maps and virtual non-contrast (VNC) images tend to suffer from significant inaccuracies and artifacts especially in low-dose spectral Computed Tomography scans.

The disadvantage of the two-scan subtraction technique is that a very accurate volumetric spatial registration is required. Although quite good registration algorithms are already available, commercially and in research, the registration results are still not accurate enough in many cases, and miss-registration artifacts exist in the subtraction results.

In addition, performing two scans requires somewhat more complicated and time consuming clinical workflow and patient planning, than just performing a single contrasted scan with spectral Computed Tomography.

A limitation in both techniques is that in order to improve the iodine map appearance, it is common in both methods to apply relatively strong filters to reduce noise and artifacts from the obtained iodine maps, these techniques often degrade significantly the map spatial resolution and the detectability of small features and structures with relatively low iodine concentration.

The purpose of the invention is to combine the best of each existing method to overcome their respective disadvantage.

SUMMARY OF THE INVENTION

The present invention relates to a method for generating contrast agent concentration map from a non-contrast enhanced Computed Tomography scan, a contrast enhanced Computed Tomography scan and corresponding spectral Computed Tomography data, comprising:

a. Generating at least two different primary contrast agent concentration maps out of the non-contrast enhanced Computed Tomography scan, the contrast enhanced Computed Tomography scan and the corresponding spectral Computed Tomography data, b. Performing a local quality analysis of each primary contrast agent concentration map c. Determining local volumetric weights for each primary contrast agent concentration map based on the local quality analysis, and d. Generating a secondary contrast agent concentration map based on the two primary contrast agent concentration maps and on their corresponding local volumetric weights.

In a preferred embodiment, at least the contrast enhanced scan is performed in a spectral Computed Tomography mode to generate both conventional contrast enhanced Computed Tomography images and spectral Computed Tomography data.

The 'local analysis' is to be understood as an analysis performed on several group of voxels which can have any size, including a size of one single voxel. The analyzed groups of voxels can form a partition of the whole contrast agent concentration map, or not. That is to say, the local analysis can concern the whole maps or only part of it. The analysis is performed so that 'local volumetric weight' may be assigned to corresponding groups of voxels. Said corresponding groups of voxels may be the same groups of voxels which underwent the 'local analysis', or a different set of group of voxels. The last step may typically consists in generating a secondary map which is a weighted average of both primary maps, said weighted average operation taking into account the calculated weights.

In a preferred embodiment, at least one of the primary contrast agent concentration maps is obtained by performing a volumetric spatial registration step and an image subtraction step out of the non-contrast enhanced Computed Tomography scan and the contrast enhanced Computed Tomography scan. The registration algorithm may utilize techniques relate to elastic, affine or rigid registration. In that case, the method may further comprise improving the volumetric spatial registration step by calculating a Virtual non-contrast image volume from the contrast enhanced Computed Tomography scan and/or the spectral Computed Tomography data, calculating a deformation function allowing to deform the non-contrast enhanced Computed Tomography scan image volume into the Virtual non-contrast image volume, and applying said deformation function to the contrast enhanced Computed Tomography scan image volume. Indeed, the spatial registration accuracy is an important limitation of the registration-subtraction way of generating a contrast agent concentration map, and it is interesting to take benefit from the available spectral data available in a clever way. Another way to improve the registration step, is to further add the steps consisting of a. improving the primary contrast agent concentration map obtained by performing a volumetric spatial registration step and an image subtraction step, using information out of another primary contrast agent concentration map, b. subtracting the contrast agent concentration map from the contrast enhanced Computed Tomography scan image volume to obtain an altered non-contrast enhanced Computed Tomography image volume, c. generating a new contrast agent concentration map by performing a volumetric spatial registration step and an image subtraction step out of the altered non-contrast enhanced Computed Tomography image volume and the contrast enhanced Computed Tomography scan image volume.

In a preferred embodiment, at least one of the primary contrast agent concentration maps is obtained out of the sole spectral Computed Tomography data.

In that case, the local quality analysis of the primary contrast agent concentration map obtained out of the sole spectral Computed Tomography data may comprise considering local radiation dose levels. For example, the local radiation dose levels may be obtained from scan parameters and tools, preferably from calculated dose maps.

Typically, at least one of the non-contrast enhanced Computed Tomography scan and the contrast enhanced Computed Tomography scan may be a low-dose scan. As a matter of fact, the primary scans are only needed, usually, for a coarse analysis so the lower dose, the better.

The local quality analysis and the corresponding local volumetric weights may be performed for each voxel of the primary contrast agent concentration maps. It actually corresponds to the case mentioned before, wherein the group of voxels which are analyzed have a size of one single voxel.

Each primary contrast agent concentration map's scale of unit may be adapted and/or normalized prior to the generation of the secondary contrast agent concentration map.

The local quality analysis of at least one of the primary contrast agent concentration map may comprise techniques such as local image noise estimation, standard deviation measurements on a group of neighbor pixels, fine structure or shape analysis, local image artifact analysis, spatial resolution analysis, local spatial frequencies or wavelength analysis, or analysis of map values or value gradients out of pre-determined limits.

A smooth transition between the local volumetric weights of each of the primary contrast agent concentration maps may be generated. Although this might increase the readability of the final map, it may blur some discontinuities such as the wall of some vessels. As such, it may be interesting to couple such functionality with a segmentation algorithm which could weigh the amount of smoothing which is relevant.

The invention also relates to a device adapted for communicating with a medical imaging device comprising:

a. a processor configured for generating at least two different primary contrast agent concentration maps out of a non-contrast enhanced Computed Tomography scan, a contrast enhanced Computed Tomography scan and corresponding spectral Computed Tomography data; performing a local quality analysis of each primary contrast agent concentration map, determining local volumetric weights for each primary contrast agent concentration map based on the local quality analysis, and generating a secondary contrast agent concentration map based on the two primary contrast agent concentration maps and on their corresponding local volumetric weights.

b. Means for displaying said secondary contrast agent concentration map.

The invention also relates to a Computed Tomography scanner comprising a device configured to implement a method according to the invention.

The invention also relates to a computer readable storage medium encoded with computer readable instructions, which, when executed by a processor, causes the processor to perform a method according to the invention.

Still further aspects and embodiments of the present invention will be appreciated by those of ordinary skill in the art upon reading and understanding the following detailed description. Numerous additional advantages and benefits will become apparent to those of ordinary skill in the art upon reading the following detailed description of preferred embodiments.

BRIEF DESCRIPTION OF THE FIGURES

The invention shall be better understood by reading the following detailed description of an embodiment of the invention and by examining the annexed drawing, on which.

The invention may take form in various components and arrangements of components, and in various process operations and arrangements of process operations. The drawings are only for the purpose of illustrating preferred embodiments and are not to be construed as limiting the invention.

To better visualize certain features may be omitted or dimensions may be not be according to scale.

DETAILED DESCRIPTION OF EMBODIMENTS

Figure 1:
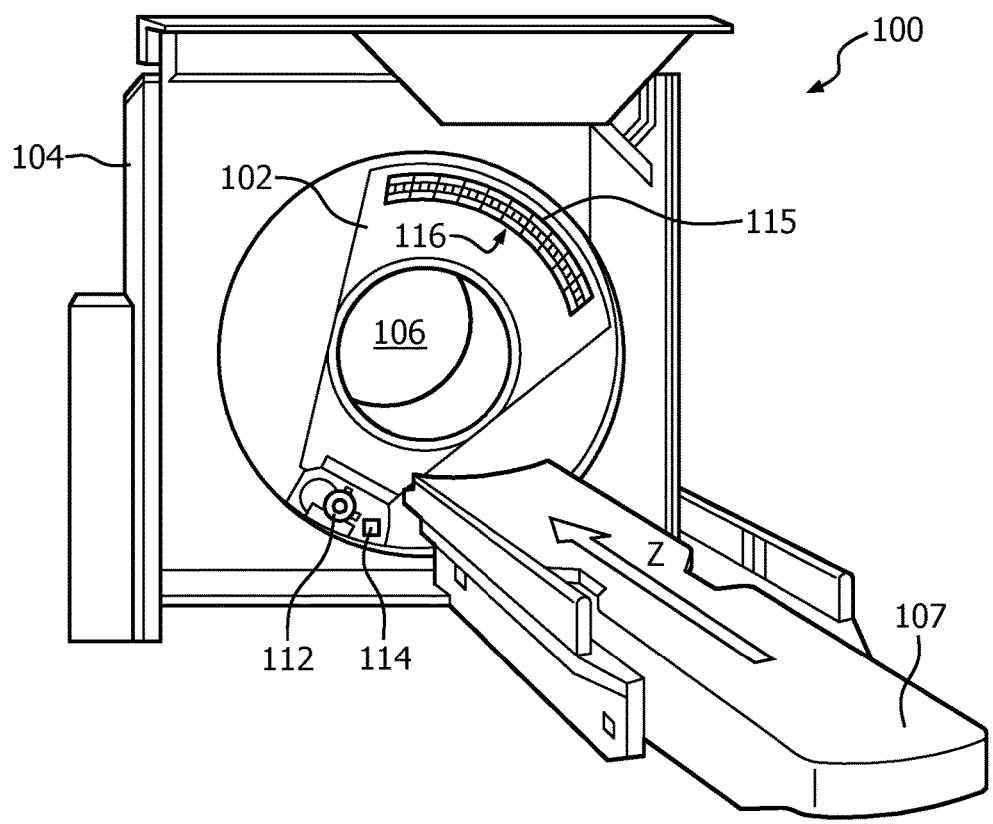
FIG. 1 is a typical or spectral Computed Tomography canner.

FIG. 1 schematically illustrates an example imaging system 100, such as a computed tomography (CT) scanner. The imaging system 100 includes a rotating gantry 102 and a stationary gantry 104. The rotating gantry 102 is rotatably supported by the stationary gantry 104. The rotating gantry 102 is configured to rotate around an examination region 106 about a longitudinal or z-axis. The imaging system 100 further includes a subject support 107 that supports a subject or object in the examination region 106 before, during and/or after scanning. The subject support 107 can also be used to load and/or unload the subject or object into or from the examination region 106. The imaging system 100 further includes a radiation source 112, such as an x-ray tube, that is rotatably supported by the rotating gantry 102. The radiation source 112 rotates with the rotating gantry 102 around the examination region 106 and is configured to generate and emit radiation that traverses the examination region 106. In one instance, the radiation source 112 is configured to switch an emission voltage between two or more emission voltages (e.g., 80 and 140 kVp, 80, 100 and 120 kVp, etc.) within an integration period and/or otherwise. In a variation, the imaging system 100 includes multiple radiation sources 112 that emit radiation at different emission voltages. In another variation, the radiation source 112 includes a single broad spectrum x-ray tube. The imaging system 100 may further include a radiation source controller 114. The radiation source controller 114 is then configured to modulate a flux of the generated radiation. For example, the radiation controller 114 can selectively change a cathode heating current of the radiation source 112, apply a charge to inhibit electron flow of the radiation source 112, filter the emitted radiation, etc. to modulate the flux. In the illustrated example, the radiation source controller 114 modulates the flux based on a predetermined modulation pattern.

The imaging system 100 further includes a one or two dimensional array 115 of radiation sensitive detector pixels 116. The pixels 116 are located opposite the radiation source 112, across the examination region 106, detect radiation traversing the examination region 106, and generate an electrical signal (projection data) indicative thereof. In one embodiment, the pixels 116 include direct conversion photon counting detector pixels. With such pixels, the generated signal includes an electrical current or voltage having a peak amplitude or a peak height that is indicative of the energy of a detected photon. The direct conversion photon counting detector pixels may include any suitable direct conversion material such as CdTe, CdZnTe, Si, Ge, GaAs or other direct conversion material.

In another embodiment, a detector array 115 subtends an angular arc opposite the examination region 106 relative to the radiation source 112. The detector array 115 detects radiation that traverses the examination region 106 and generates a signal (projection data) indicative thereof. Where the radiation source voltage is switched between at least two emission voltages and/or two or more x-ray tubes emit radiation at two different emission voltages, the detector array 115 generates a signal for each of the radiation source voltages. For a single broad spectrum x-ray tube, the detector array 115 includes an energy-resolving detector (e.g., multi-layered scintillator/photodiode, a direct conversion photon counting, etc.) that produces the signals.

A reconstruction processor reconstructs the signal with one or more spectral bases decomposition algorithms stored in reconstruction algorithm memory or elsewhere. The reconstruction processor, employing at least one of the algorithms, produces the spectral volumetric image data including two or more sets of volumetric image data corresponding to different image bases. For example, with dual energy these bases can be photo electric/Compton scatter pairs, water/iodine pairs (or other material base pairs), two different effective keV x-ray energy pairs, etc. In another example, with photon counting CT, the reconstruction processor can generate two or more image bases, including a k-edge image basis, e.g., where there are three or more energy windows. The reconstruction processor may also generate non-spectral volumetric image data.

Figure 2:
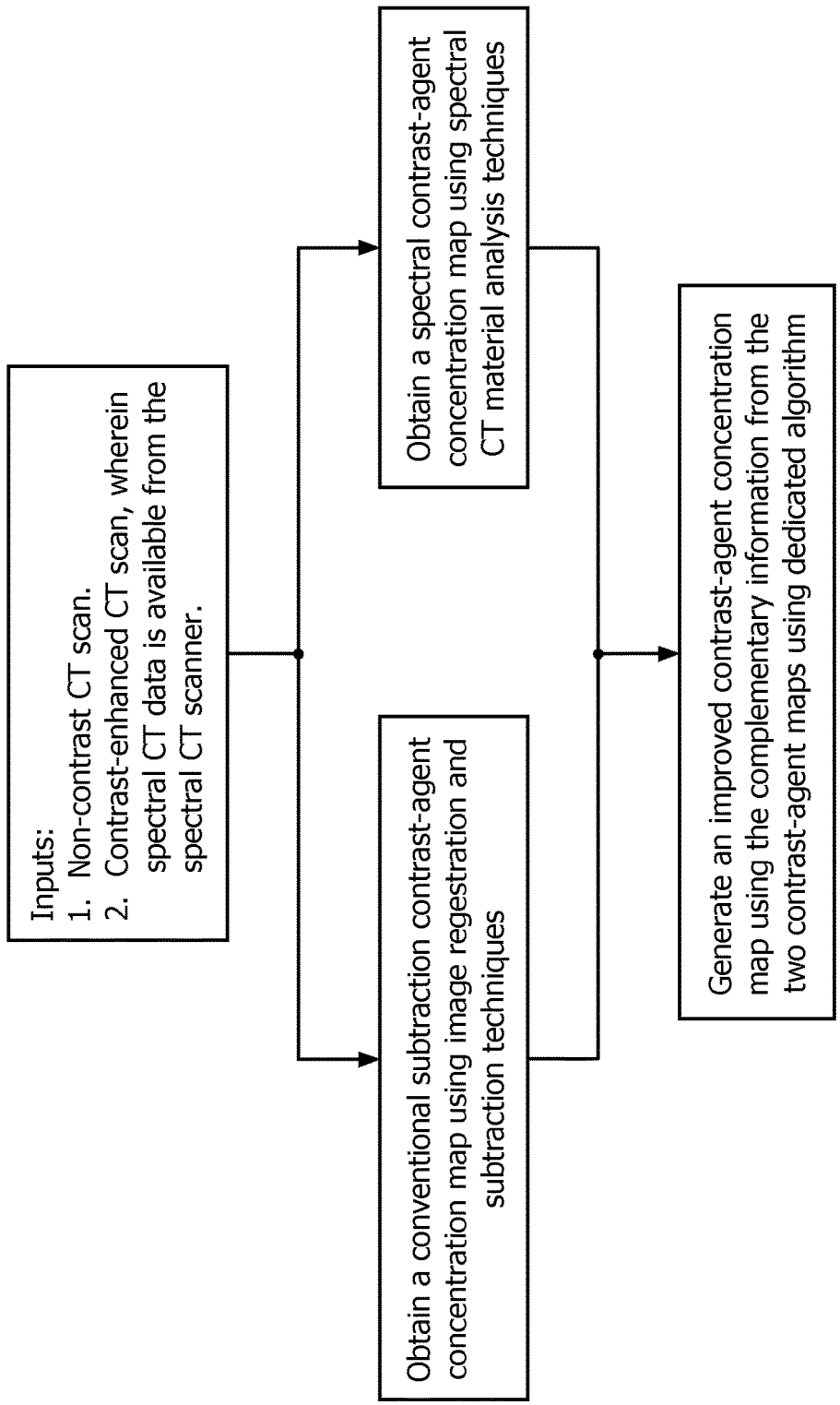
FIG. 2 represents a general flowchart of a method according to a preferred embodiment of the invention.

FIG. 2 is a general flowchart of a preferred embodiment according to the invention. It is a method for utilizing a spectral CT scanner in an optimal way, especially in clinical situations where high quality iodine maps are required in addition to fully diagnostic non-contrast images. The method may be especially relevant in low-dose scans where spectral CT results may sufferer from degraded quality. The key idea is to combine the complementary information from the registration-subtraction technique and from the spectral analysis technique in order to provide a better iodine-map than of what can be achieved from any of the two methods separately. From the input Non-contrast enhanced Computed Tomography scan and contrast-enhanced Computed Tomography and the corresponding spectral data available, two contrast agent, e.g; iodine, concentration maps are obtained. The first map through the conventional subtraction-registration method whereas the second maps is derived from the spectral data. Both methods have been described in the introduction part. Eventually, the two maps are combined to generate a secondary contrast agent concentration map. This step is further detailed in FIGS. 7 and 8.

Figure 3:
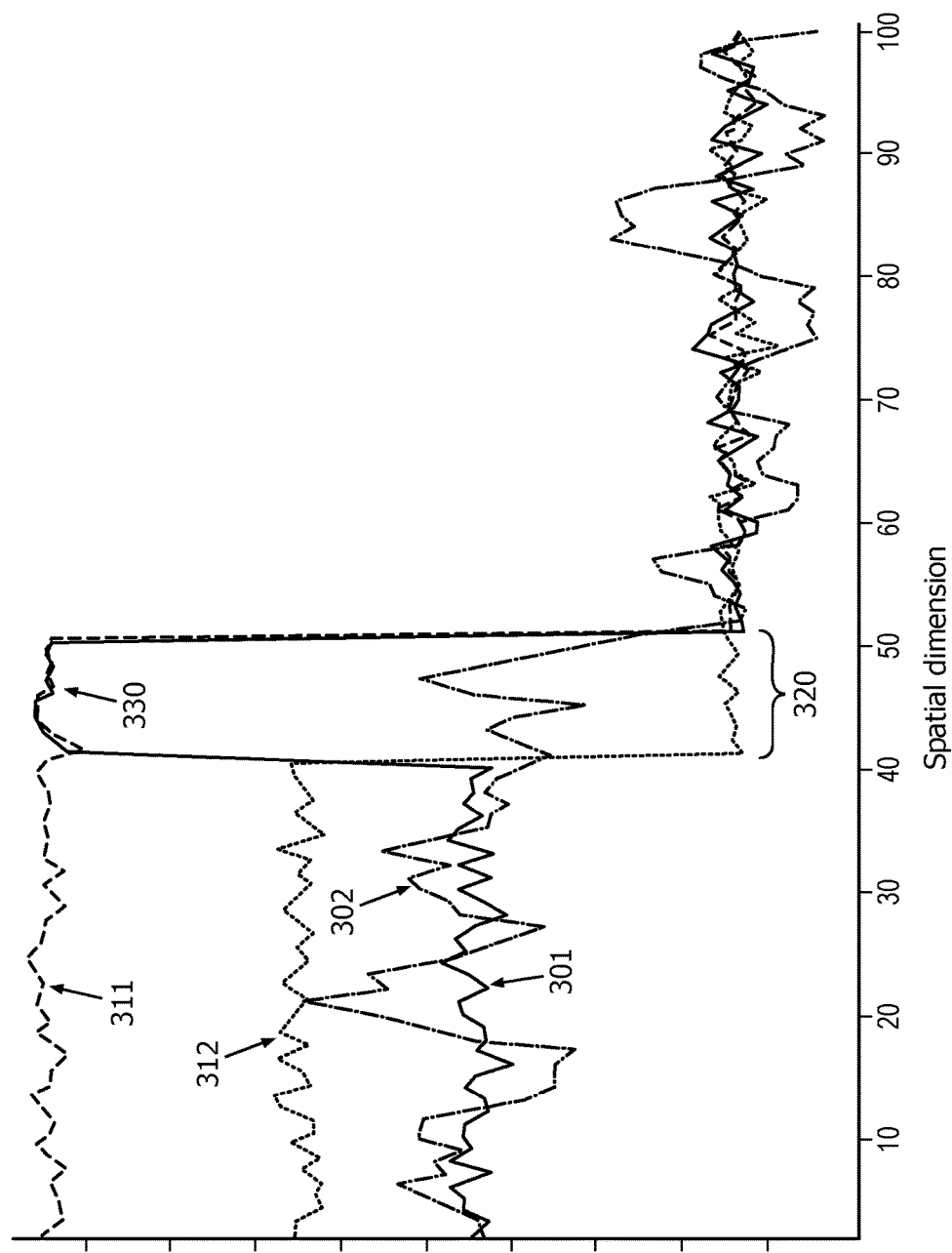
FIG. 3 represents the image intensity of the primary contrast agent concentration maps of FIG. 2.

FIG. 3 demonstrates the fundamental differences between contrast agent maps derived from the two techniques (only 1D image profile is shown for clarity). The curve 301 is the result of the registration-subtraction map, with remaining miss-registration artifact 330 which introduces large error in a localized region. In other regions where the registration is fine, the contrast agent map shows good quality. The dotted curves 311 and 312 correspond respectively the contrasted and non-contrasted images which have been used for calculating the curve 301. As the curve 312 have been miss-registered, the spatial miss-registration shift 320 causes an important artefact 330.

The curve 302 is the result of the spectral analysis derived only from the contrasted scan. There are no local sharp artifacts, however the overall noise is significantly higher, including some low frequency noise that may be interpreted as real structures.

The aim in the proposed method, regarding this illustration, is to generate an optimized and improved curve from the two insufficient-quality curves.

Figure 4:
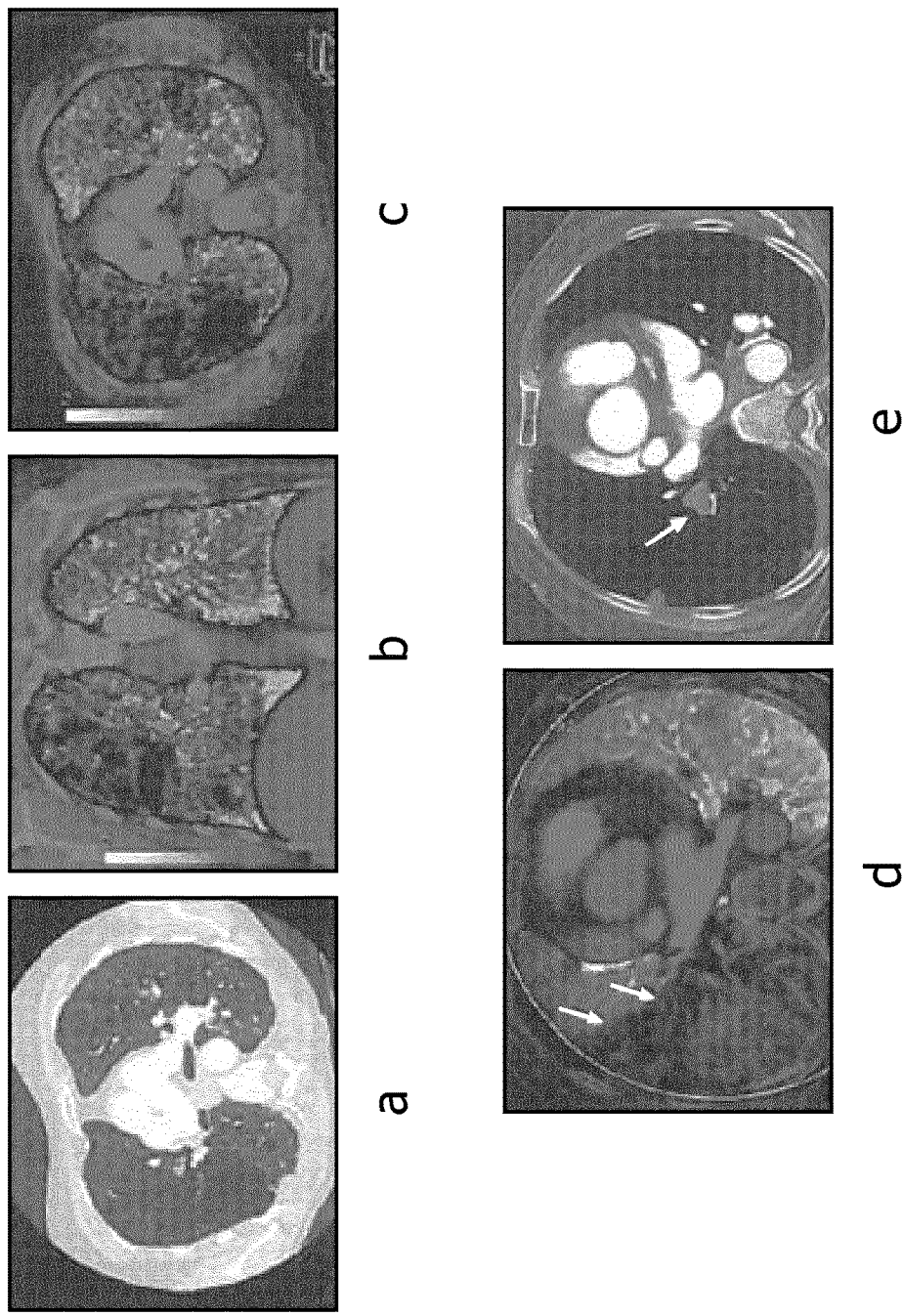
FIG. 4 shows clinical example of primary contrast agent concentration maps obtained according to the method of FIG. 2, FIGS. 5 and 6 are flowcharts representing two ways of improving the spatial registration accuracy to obtain one of the primary contrast agent concentration of the method of FIG. 2, and FIGS. 7 and 8 are flowcharts further detailing the combination step of the method according to FIG. 2.

Corresponding clinical example of contrast agent concentration maps are shown on FIG. 4. FIGS. 4a, 4b, and 4c show example of iodine concentration maps obtained from conventional Computed Tomography scans through the registration-subtraction techniques. FIGS. 4d and 4e show example of iodine concentration maps obtained from spectral dual-energy Computed Tomography scans.

In one aspect of the invention spatial-registration accuracy of the contrast agent concentration map obtained through the registration-subtraction method can be improved. Spatial registration problems between the preand post-contrast scans are sometimes affected by the image inconsistency due to the changes in local Hounsfield Unit (HU) after the contrast agent administration. Spectral Computed Tomography can assist in performing more accurate registration by using images showing virtually non-contrast enhancement, where they are derived from the actually contrasted scan; or otherwise by correcting the registration artifacts in an iterative scheme. The two options are shown in the flowcharts of FIG. 5 and FIG. 6.

Figure 5:
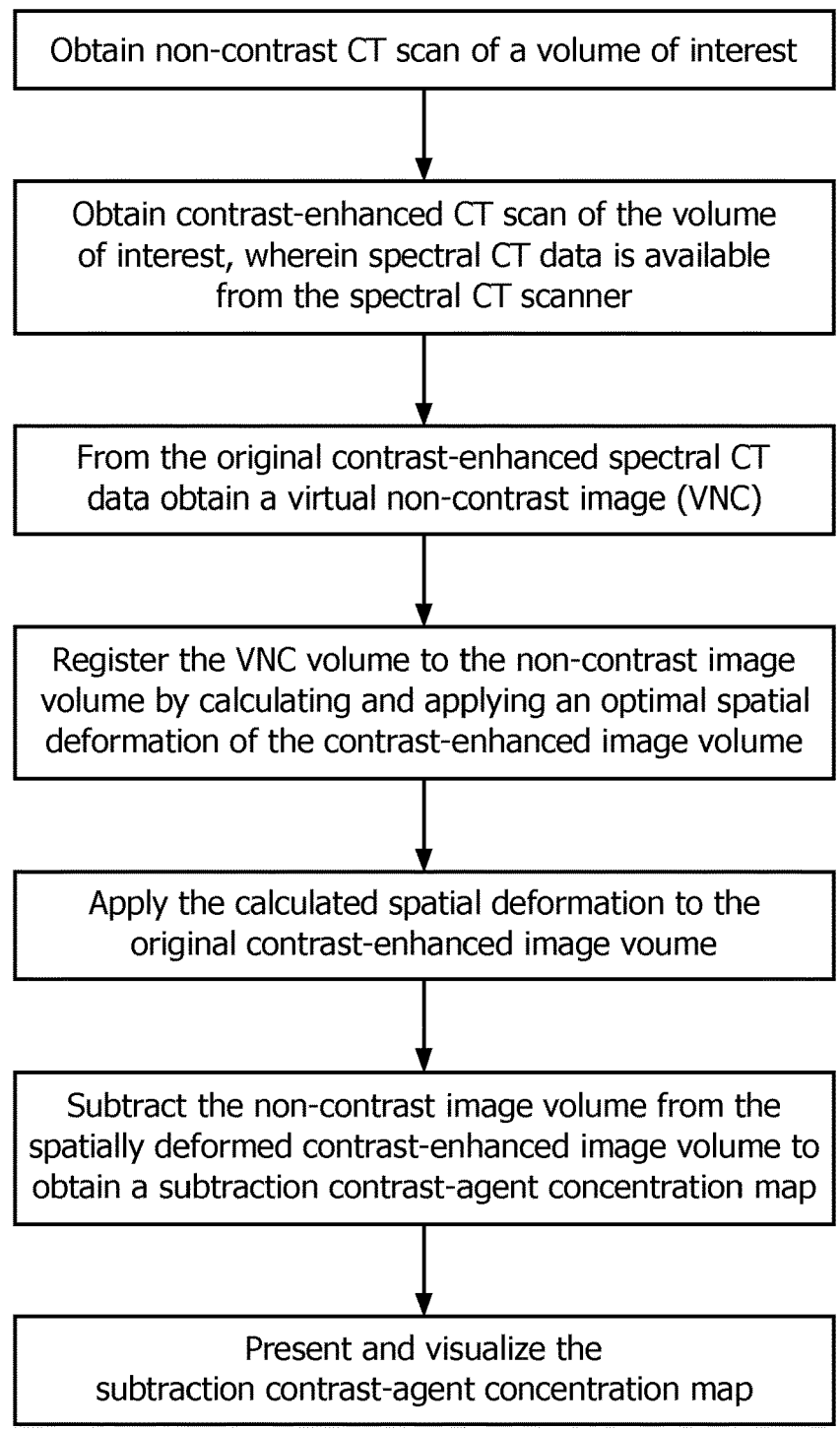

In FIG. 5, the spectral virtual non-contrast image (VNC) volume, which is calculated first, is used to improve the registration accuracy for the process of registration subtraction map. This option may be especially suited if the spectral Computed Tomography system in use provides high quality VNC results, or in clinical protocols where very large HU variations exist between the pre and post contrast scans due to high contrast agent concentration.

Figure 6:
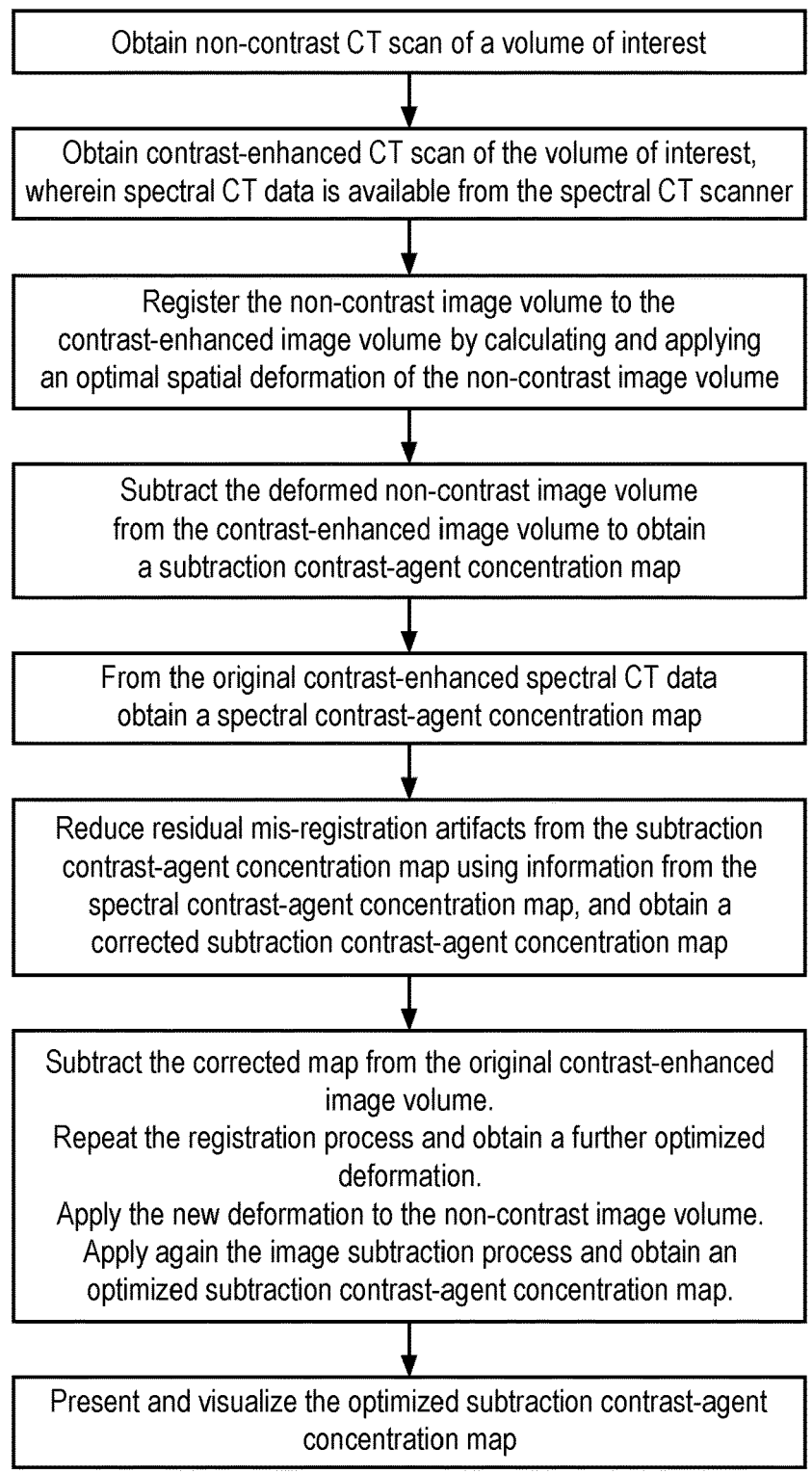

In FIG. 6, the initial registration-subtraction map is corrected using information from the spectral map. The corrected registration-subtraction map is subtracted from the contrasted image to form a kind of "conventional" virtual non-contrast map, which is registered with the pre-contrast image volume. The virtual elimination of the contrast agent enhancement can assist in better registration results. The improved deformation field is used to generate an improved registration-subtraction map, which will be used as the final map. It is interesting to point out that in this scheme the spatial registration is performed as a two iterations process.

Figure 7:
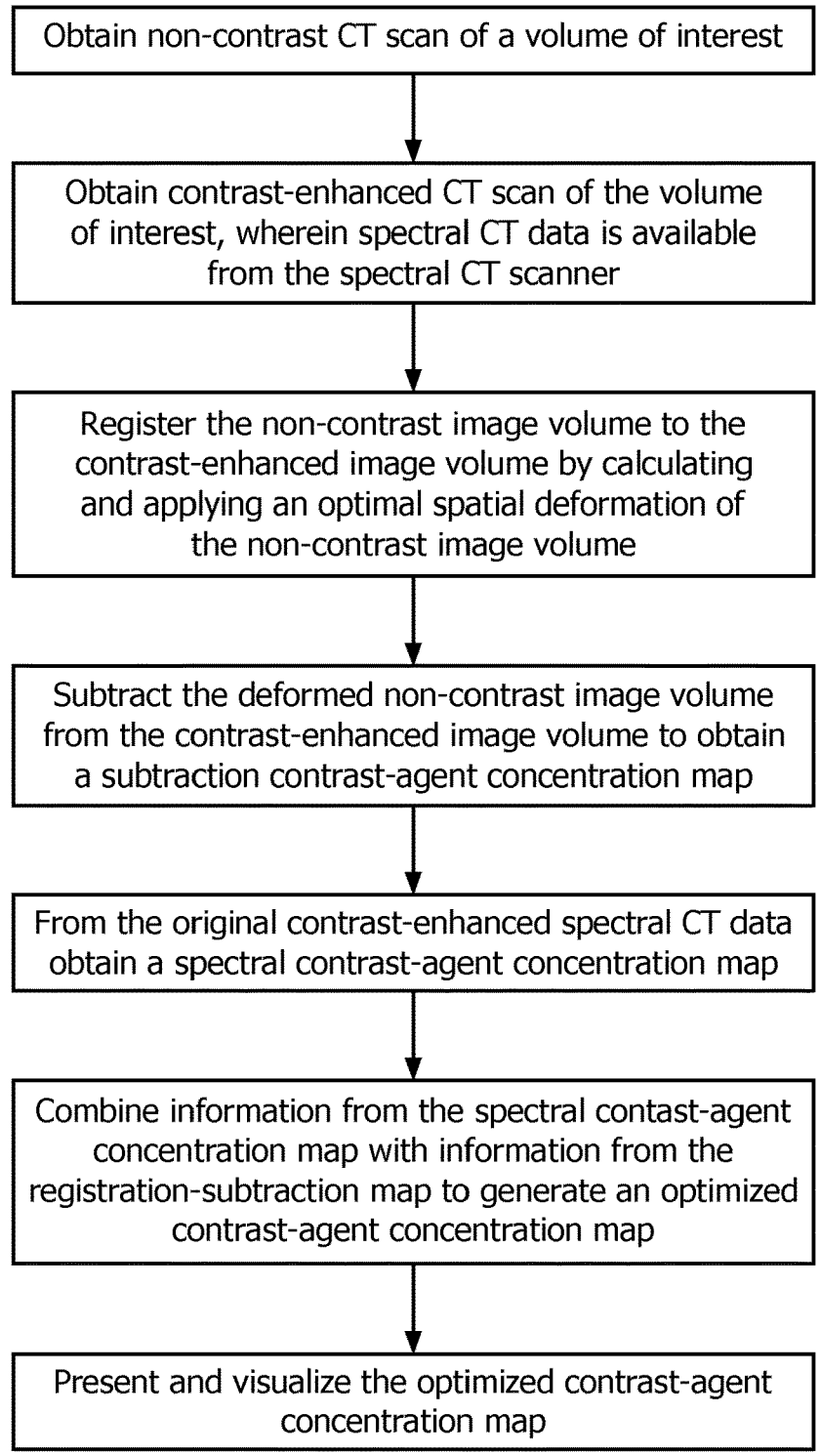
Figure 8:
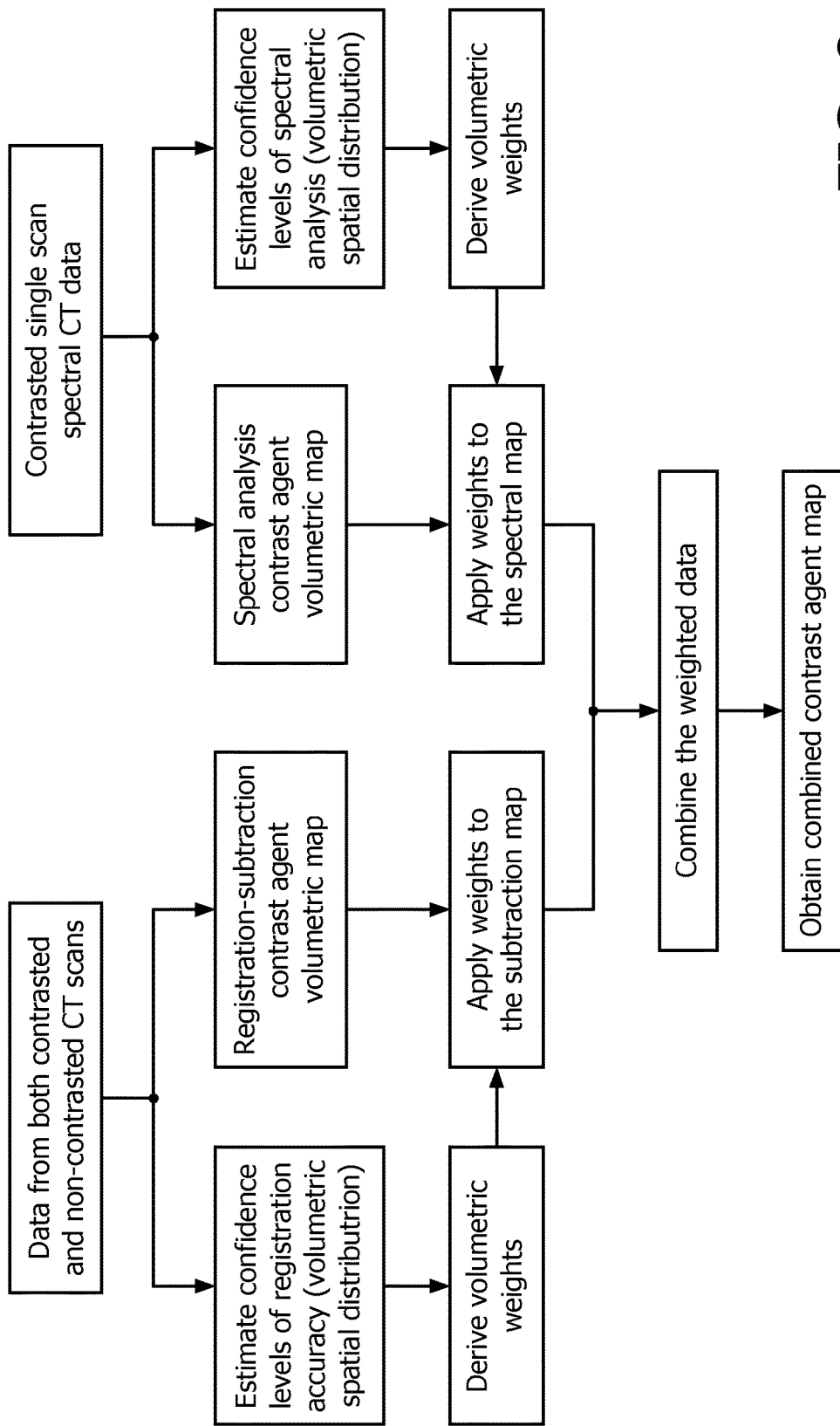

FIG. 7 and FIG. 8 illustrate the method steps of optimally combining the two map types. In FIG. 7, a registration-subtraction map as well as a spectral map are first calculated independently. A combined contrast agent concentration map is directly generated using complementary information from the registration-subtraction map and from the spectral map. The block in the bold frame is further detailed in FIG. 8.

The flowchart of FIG. 8 shows an option how to generate combined contrast agent map by weighting the values from the registration-subtraction map and from the spectral map. The key point is that for each one of the two maps an analysis of the local map quality is made and volumetric weights are derived accordingly. For example, if in one map the local map quality is low and in the second map the local quality is high, the combination weights will favor the map with the high quality. The wording "local" may describe each image pixel or a group of pixels or voxels, or an otherwise determined region of interest.

As an option, the scales or units of the maps from the two methods can be adapted or normalized prior to the combination.

The local confidence level of spatial registration accuracy in CT can be assessed by several known techniques such as the method published in:

'Supervised quality assessment of medical image registration: Application to intra-patient CT lung registration', S. E. Muenzing et al., *Medical Image Analysis*, December 2012.

The local confidence level of spectral analysis can be assessed by considering the known and pre-measured system limitations with respect to radiation dose levels and ranges of the contrast agent concentrations. The local dose levels can be obtained from the scan parameters and tools such as calculated dose maps.

As an option, a smooth transition between weights of the two maps may be generated by special smoothing of the two weight distributions.

While the invention has been illustrated and described in detail in the drawings and foregoing description, such illustration and description are to be considered illustrative or exemplary and not restrictive; the invention is not limited to the discussed embodiments.

Other variations to the disclosed embodiments may be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A method for generating contrast agent concentration map from a non-contrast enhanced Computed Tomography scan, a contrast enhanced Computed Tomography scan and corresponding spectral Computed Tomography data, comprising:
   a. Generating at least two different primary contrast agent concentration maps out of the non-contrast enhanced Computed Tomography scan, the contrast enhanced Computed Tomography scan and the spectral Computed Tomography data,
   b. Performing a local quality analysis of each primary contrast agent concentration map
   c. Determining local volumetric weights for each primary contrast agent concentration map based on the local quality analysis, and
   d. Generating a new contrast agent concentration map based on the two primary contrast agent concentration maps and on their corresponding local volumetric weights.

2. The method according to claim 1, wherein at least one of the primary contrast agent concentration maps is obtained by performing a volumetric spatial registration step and an image subtraction step out of the non-contrast enhanced Computed Tomography scan and the contrast enhanced Computed Tomography scan.

3. The method according to claim 2 comprising improving the volumetric spatial registration step by calculating a Virtual non-contrast image volume from the contrast enhanced Computed Tomography scan and/or the spectral Computed Tomography data, calculating a deformation function allowing to deform the non-contrast enhanced Computed Tomography scan into the Virtual non-contrast image volume, and applying said deformation function to the contrast enhanced Computed Tomography scan.

4. The method according to claim 2, comprising:
   a. improving the primary contrast agent concentration step obtained by performing a volumetric spatial registration step and an image subtraction step, using information out of another primary contrast agent concentration map,
   b. subtracting one of the primary contrast agent concentration map from the contrast enhanced Computed Tomography scan to obtain an altered non-contrast enhanced Computed Tomography scan,
   c. generating the new contrast agent concentration map by performing a volumetric spatial registration step and an image subtraction step out of the altered non-contrast enhanced Computed Tomography scan and the contrast enhanced Computed Tomography scan.

5. The method according to claim 1, wherein at least one of the primary contrast agent concentration maps is obtained out of the sole spectral Computed Tomography data.

6. The method according to claim 1, wherein the local quality analysis of the primary contrast agent concentration map obtained out of the sole spectral Computed Tomography data comprises considering local radiation dose levels.

7. The method according to claim 6, wherein the local radiation dose levels are obtained from scan parameters and tools.

8. The method according to claim 1, wherein at least one of the non-contrast enhanced Computed Tomography scan, and the contrast enhanced Computed Tomography scan is a low-dose scan.

9. The method according to claim 1, wherein the local quality analysis and the corresponding local volumetric weights are performed for each voxel of the primary contrast agent concentration maps.

10. The method according to claim 1, wherein each primary contrast agent concentration map's scale of unit is adapted and/or normalized prior to the generation of the new contrast agent concentration map.

11. The method according to claim 1, wherein the local quality analysis of at least one of the primary contrast agent concentration map comprises techniques chosen among local image noise estimation, standard deviation measurements on a group of neighbor pixels, fine structure or shape analysis, local image artifact analysis, spatial resolution analysis, local spatial frequencies or wavelength analysis, or analysis of map values or value gradients out of predetermined limits.

12. The method according to claim 1, wherein a smooth transition between the local volumetric weights of each of the primary contrast agent concentration maps is generated.

13. A device adapted for communicating with a medical imaging device comprising:
   a. a processor configured for generating at least two different primary contrast agent concentration maps out of a non-contrast enhanced Computed Tomography scan, a contrast enhanced Computed Tomography scan and corresponding spectral Computed Tomography data; performing a local quality analysis of each primary contrast agent concentration map, determining local volumetric weights for each primary contrast agent concentration map based on the local quality analysis, and generating a new contrast agent concentration map based on the two primary contrast agent concentration maps and on their corresponding local volumetric weights,
   b. Means for displaying said new contrast agent concentration map.

14. A computed Tomography scanner comprising a device configured to implement a method according to claim 1.

15. A computer non-transitory readable storage medium encoded with computer readable instructions, which, when executed by a processor, causes the processor to perform a method according to claim 1.

* * * * *